US009329124B2

(12) United States Patent
Ito

(10) Patent No.: US 9,329,124 B2
(45) Date of Patent: May 3, 2016

(54) SCATTERED LIGHT MEASUREMENT APPARATUS

(71) Applicant: OLYMPUS CORPORATION, Tokyo (JP)

(72) Inventor: Ryosuke Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/638,167

(22) Filed: Mar. 4, 2015

(65) Prior Publication Data

US 2015/0177134 A1    Jun. 25, 2015

Related U.S. Application Data

(63) Continuation of application No. PCT/JP2013/074286, filed on Sep. 9, 2013.

(60) Provisional application No. 61/699,539, filed on Sep. 11, 2012.

(51) Int. Cl.
*G01N 21/55*       (2014.01)
*G01N 21/47*       (2006.01)
(Continued)

(52) U.S. Cl.
CPC .......... *G01N 21/474* (2013.01); *A61B 1/00167* (2013.01); *A61B 1/042* (2013.01); *A61B 1/07* (2013.01); *G01N 2021/475* (2013.01); *G01N 2021/4745* (2013.01)

(58) Field of Classification Search
CPC   G01N 21/1702; G01N 21/211; G01N 21/274
USPC ......... 356/128–130, 361, 365, 303, 370, 446, 356/336
See application file for complete search history.

(56) References Cited

U.S. PATENT DOCUMENTS

2005/0242298 A1    11/2005  Genet et al.
2008/0062401 A1*   3/2008   Bakker et al. .......... G01N 21/65
                                                              356/51

(Continued)

FOREIGN PATENT DOCUMENTS

JP    2005532883 A    11/2005
JP    2011504782 A    2/2011

(Continued)

OTHER PUBLICATIONS

Oct. 8, 2013 International Search Report issued in International Application No. PCT/JP2013/074286.

(Continued)

*Primary Examiner* — Kara E Geisel
*Assistant Examiner* — Iyabo S Alli
(74) *Attorney, Agent, or Firm* — Oliff PLC

(57)    ABSTRACT

A scattered light measurement apparatus includes an optical measurement apparatus, and a scattered light measurement probe configured to irradiate an object with light from the optical measurement apparatus, configured to receive light from the object, and configured to output the received light to the optical measurement apparatus. The optical measurement apparatus includes: a light source configured to emit light including at least light of a measurement target wavelength; first and second optical detectors configured to detect the light received by the scattered light measurement probe; a branching unit configured to guide the light from the light source to the scattered light measurement probe and guide the light from the scattered light measurement probe to the first and second optical detectors; and a control unit configured to evaluate scattering characteristics of a surface layer of the object based on the light detected by the first and second optical detectors.

4 Claims, 7 Drawing Sheets

(51) Int. Cl.
  *A61B 1/00* (2006.01)
  *A61B 1/04* (2006.01)
  *A61B 1/07* (2006.01)

(56) References Cited

U.S. PATENT DOCUMENTS

| 2009/0009759 A1* | 1/2009 | Backman et al. .. A61B 1/00096 356/303 |
| 2012/0101372 A1 | 4/2012 | Teramura et al. |
| 2013/0329224 A1 | 12/2013 | Takaoka et al. |

FOREIGN PATENT DOCUMENTS

| JP | 2012157384 A | 8/2012 |
| WO | 2009070160 A1 | 6/2009 |
| WO | 2012057151 A1 | 5/2012 |

OTHER PUBLICATIONS

Kim et al., "Low-Coherence enhanced Back Scattering: Review of Principles and Applications for Colon Cancer Screening," Journal of Biomedical Optics, Jul./Aug. 2006, vol. 11, No. 4, pp. 041125-1 through 041125-10.

Turzhitsky et al., "Characterization of Light Transport in Scattering Media at Subdiffusion Length Scales with Low-Coherence Enhanced Backscattering," IEEE Journal of Selected Topics in Quantum Electronics, May/Jun. 2010, vol. 16, No. 3, pp. 619-626.

Roy et al., "Association Between Rectal Optical Signatures and Colonic Neoplasia: Potential Applications for Screening," Cancer Research, May 15, 2009, vol. 69, No. 10, pp. 4476-4483.

* cited by examiner

SCATTERED LIGHT MEASUREMENT APPARATUS

CROSS-REFERENCE TO RELATED APPLICATIONS

This application is a continuation of PCT international application Ser. No. PCT/JP2013/074286 filed on Sep. 9, 2013 which designates the United States, incorporated herein by reference, and which claims the benefit of priority from U.S. provisional application No. 61/699,539 filed on Sep. 11, 2012, incorporated herein by reference.

BACKGROUND

1. Technical Field

The disclosure relates to a scattered light measurement apparatus for measuring information on an internal structure of an object to be measured, as an amount of scattering and absorption of light.

2. Related Art

Conventionally, backscattered light returned from a relatively weak scattering medium such as a biological tissue is detected as interference enhanced light according to a degree of spatial coherence of light illuminating the scattering medium (see Non-Patent Literature 1). A spectroscopic information measuring technique that uses this phenomenon is called low-enhanced backscattering spectroscopy (LEBS) and characteristics of interference patterns with respect to a scattering mean free path (an inverse of a scattering coefficient) ls* in the scattering medium have been well studied (see Non-Patent Literature 2). This scattering mean free path ls* has a correlation with an internal structure change in the scattering medium, and is used to detect a minute change in a tissue structure such as that found in cancer in an early stage. It has also been known that discrimination of colon cancer is possible using interference patterns of returning scattered light (see Non-Patent Literature 3).

In the LEBS described above, a technique applied to non-invasive measurement in a human body performed through a small diameter probe inserted in an endoscope is known (see Patent Literature 1). In this technique, to obtain an interference pattern, detection fibers are arranged at a plurality of different positions (corresponding to different scattering angles) on a plane where an interference pattern is formed and signals are detected by corresponding detectors.

Furthermore, in the LEBS, detection of backscattered light from a scatterer surface layer under limiting condition is performed, and a detection depth in the scatterer surface layer is controlled by a spatial coherence length. FIG. 13 is a schematic diagram illustrating main elements of a scattered light measurement probe, which is a conventional small diameter probe. A scattered light measurement probe 200 illustrated in FIG. 13 includes an illumination fiber 201 that emits illumination light to an object to be measured (scatterer surface layer 300), a plurality of detection fibers 202a to 202c on which returned light of the illumination light reflected and/or scattered by the object to be measured is incident at different angles, and an optical element 210 provided at tips of the illumination fiber 201 and the detection fibers 202a to 202c.

The optical element 210 is cylindrically shaped and is formed of a transmissive glass having a specified refractive index. When the measurement is performed, a tip of the optical element 210 comes in contact with the scatterer surface layer 300, so that a distance from the illumination fiber 201 and the detection fibers 202a to 202c to the object to be measured is fixed.

In this case, the detection depth D100 of the scatterer 300 is defined by a spatial coherence length Lsc. The spatial coherence length Lsc satisfies a relation of formula (1) below when a length of the optical element 210 in a central axis direction of the cylinder is R, the refractive index of the optical element 210 is n, the diameter of the illumination fiber 201 is ρ, and the wavelength of the light emitted from the illumination fiber 201 (light source) is λ.

$$Lsc = \lambda R / \pi \rho n \quad (1)$$

In the scattered light measurement probe 200, R and ρ are set so that the spatial coherence length Lsc becomes of a sufficiently smaller value than the scattering mean free path ls*.

CITATION LIST

Patent Literature

Patent Literature 1: United States Patent Application Publication No. 2009/0009759

Non-Patent Literature

Non-Patent Literature 1: Young L. Kim, et al, "Low-coherence enhanced backscattering: review of principles and applications for colon cancer screening" Journal of Biomedical Optics, 11(4), 041125 2006

Non-Patent Literature 2: V, Turzhitsky, et al, "Characterization of Light transport in Scattering Media at Subdiffusion Length Scales with Low-Coherence Enhanced Backscattering" IEEE journal of selected topics in quantum electronics, Vol. 16, No. 3, 619 (2010)

Non-Patent Literature 3: Hemant K. Roy, et al, "Association between Rectal Optical Signatures and Colonic Neoplasia: Potential Applications for Screening" Cancer Research, 69(10), 4476 (2009)

SUMMARY

In some embodiments, a scattered light measurement apparatus includes: an optical measurement apparatus to and from which light is input and output and which is configured to perform measurement of input light; and a scattered light measurement probe configured to irradiate an object to be examined with light from the optical measurement apparatus, configured to receive light from the object to be examined, and configured to output the received light to the optical measurement apparatus. The optical measurement apparatus includes: a light source configured to emit light including at least light of a measurement target wavelength; first and second optical detectors configured to detect the light received by the scattered light measurement probe; a branching unit configured to guide the light from the light source to the scattered light measurement probe and guide the light from the scattered light measurement probe to the first and second optical detectors; and a control unit configured to evaluate scattering characteristics of a surface layer of the object to be examined based on the light detected by the first and second optical detectors. The scattered light measurement probe includes: a first fiber that is connected to the optical measurement apparatus at one end thereof, configured to propagate the light from the light source to irradiate the object to be examined, configured to come in contact with the object to be examined at other end thereof, configured to receive the light that has irradiated the object to be examined, propagated inside the object to be examined, and returned thereto, and configured to guide the received light as an optical signal to the first optical detector through the branching unit; and a second fiber configured to receive the light that has been irradiated by the first fiber, propagated inside the object to be examined, and returned thereto, and configured to guide the received light as an optical signal to the second optical detector through the branching unit. The first fiber includes an approximately-rod-shaped core that is configured to propagate light and has a diameter determined according to a detection depth of the object to be examined, and the control unit is configured to evaluate the scattering characteristics based on signal intensities of the optical signal detected by the first optical detector and the optical signal detected by the second optical detector.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the invention (hereinafter referred to as "embodiments") will be described below with reference to the drawings. The present invention is not limited by the embodiments. The same reference signs are used to designate the same elements throughout the drawings. Note that the drawings are schematic and a relationship between the thickness and the width of each component, a ratio of each component, and the like are different from those of the actual components. There are dimensional differences and ratio differences between the drawings.

First Embodiment

Figure 1:
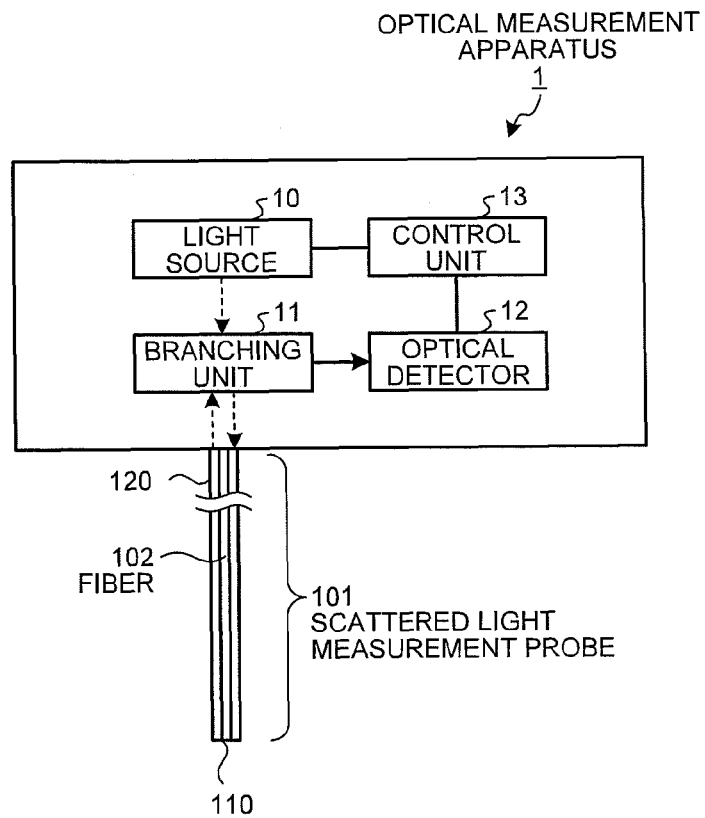
FIG. 1 is a conceptual diagram illustrating an optical measurement apparatus and a scattered light measurement probe according to a first embodiment of the present invention.
Figure 2:
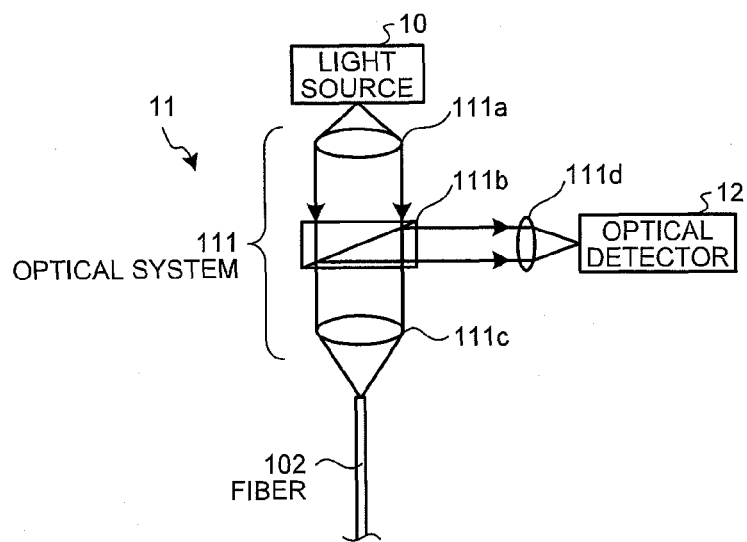
FIG. 2 is a schematic diagram illustrating a configuration of a main part of the optical measurement apparatus according to the first embodiment of the present invention.

FIG. 1 is a schematic diagram illustrating a configuration of an optical measurement apparatus 1 and a scattered light measurement probe 101 according to a first embodiment. FIG. 2 is a schematic diagram illustrating a configuration of a main part of the optical measurement apparatus 1 according to the first embodiment. A scattered light measurement apparatus includes the optical measurement apparatus 1 and the scattered light measurement probe 101.

As illustrated in FIG. 1, the scattered light measurement apparatus including the optical measurement apparatus 1 and the scattered light measurement probe 101 non-invasively detects back-scattered return light from a relatively weak scattering medium such as a biological tissue as information.

The optical measurement apparatus 1 includes a light source 10 that emits light including at least light of measurement target wavelength, a branching unit 11 that concentrates or refracts light from the light source 10 and the scattered light measurement probe 101 and guides the light in a specified direction respectively, an optical detector 12 that detects light which is received by the scattered light measurement probe 101 through the branching unit 11, and a control unit 13 that controls the entire optical measurement apparatus 1 and evaluates scattering characteristics of an object to be examined on the basis of the light detected by the optical detector 12.

The light source 10 is realized by using an incoherent light source such as a white light emitting diode (LED), a xenon lamp, a tungsten lamp, and a halogen lamp, or a coherent light source such as laser.

The branching unit 11 includes an optical system 111 to guide the light from the light source 10 to the scattered light measurement probe 101 by concentrating or refracting the light and guide the light from the object to be examined to the optical detector 12. The optical system 111 is realized by using one or a plurality of lenses, for example, a condenser lens, a collimator lens, and the like.

Specifically, as illustrated in FIG. 2, included are a lens 111a that collimates the light from the light source 10 to produce collimated light, a half mirror 111b that transmits at least a part of the collimated light from the lens 111a and reflects at least a part of light from a fiber 102 of the scattered light measurement probe 101 to the optical detector 12, a mirror 111c that collects the light from the light source 10 which passes through the half mirror 111b and guides the light to the fiber 102, and a mirror 111d that collects the light from the fiber 102 which is reflected by the half mirror 111b and guides the light to the optical detector 12. Light having at least one spectral component for irradiating the object to be examined is output from the light source 10 and the optical system 111. A circulator may be used as the optical system 111.

The optical detector 12 receives and detects illumination light which is emitted from the scattered light measurement probe 101 and propagates inside the object and returns as scattered light. The optical detector 12 is realized by using a spectrometry device, a light receiving sensor, or the like. An optical signal detected by the optical detector 12 is stored by the control unit 13 as a signal (signal intensity) necessary for measurement.

The control unit 13 includes a CPU (Central Processing Unit) and the like. The control unit 13 controls processing operations of each component of the optical measurement apparatus 1. The control unit 13 controls operations of the optical measurement apparatus 1 by transmitting instruction information and data corresponding to each component of the optical measurement apparatus 1. The control unit 13 evaluates the scattering characteristics of the object to be examined on the basis of the light detected by the optical detector 12.

The optical measurement apparatus 1 may include a recording unit that records various programs to operate the optical measurement apparatus 1 and various data and parameters used for an optical measuring process. The recording unit is realized by using a volatile memory or a non-volatile memory provided inside the optical measurement apparatus 1, a memory card that can be attached to and detached from the optical measurement apparatus 1, or the like.

Figure 3:
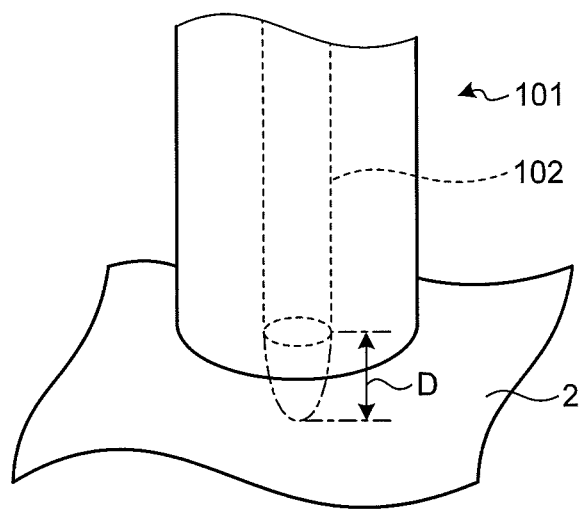
FIG. 3 is a schematic diagram illustrating a main part of the scattered light measurement probe according to the first embodiment of the present invention.
Figure 4:
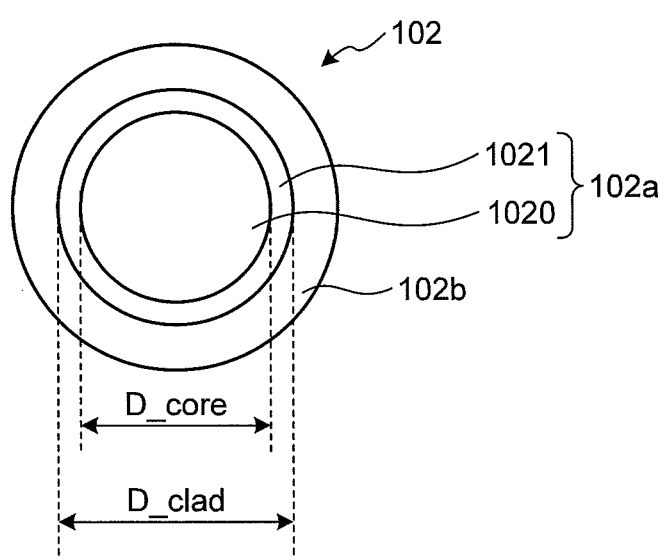
FIG. 4 is a plan view schematically illustrating an arrangement of a fiber of the scattered light measurement probe according to the first embodiment of the present invention.

FIG. 3 is a schematic diagram illustrating a main part of the scattered light measurement probe 101 according to the first embodiment. FIG. 4 is a plan view schematically illustrating an end face of the fiber 102 of the scattered light measurement probe 101 according to the first embodiment. The scattered light measurement probe 101 has a flexible tube shape. The scattered light measurement probe 101 comes in contact with a surface layer 2 of the objet to be examined (scatterer surface layer), emits light and receives light (backward scattering light) from the surface layer 2 of the objet to be examined.

The scattered light measurement probe 101 includes the fiber 102 which is provided inside the tube shape, connected to the optical measurement apparatus 1 at a far end 120, irradiates the object to be examined with at least light of measurement target wavelength from a near end 110, receives light, which is irradiated, propagates inside the object to be examined, and returns as scattered light, at the near end 110, and guides the light to the optical detector 12 as an optical signal. The fiber 102 is formed by using, for example, a step index multi-mode fiber. That is, the fiber 102 propagates illumination light as well as detected light.

As illustrated in FIG. 4, the fiber 102 includes a core 1020 which is approximately rod shaped and propagates light, a light propagating portion 102*a* including an outer layer 1021 (clad) which covers the circumference of the core 1020 and has a refractive index smaller than that of the core 1020, and a coating portion 102*b* that covers the side surface of the outer layer 1021. In FIG. 4, D_core represents the diameter of the core and D_clad represents the clad diameter of the outer layer 1021.

Here, the depth (detection depth) D of the surface layer 2 of the object to be examined can be limited based on the core diameter D_core described above because a portion for emitting light for irradiating the object to be examined and a portion for receiving the scattered light are common in the fiber and the tip of the fiber comes in contact with the object to be examined.

The detection depth D is designed in association with the spatial coherence length Lsc given by the formula (1), based on the core diameter D_core.

Thereby, it is possible to control the detection depth D without controlling the two parameters, the length R and the diameter ρ as described in the above formula (1). Here, the core diameter D_core is a fixed value as the diameter of the core 1020 of the fiber 102, so that a conventional shift of the detection depth due to an arrangement error in the fiber does not occur. Therefore, it is possible to accurately evaluate the scattering characteristics of the object to be examined on the basis of the light detected by the optical detector 12.

According to the first embodiment described above, the core diameter D_core of the fiber 102, which irradiates the object to be examined with at least light of measurement target wavelength, receives light, which is irradiated, propagates inside the object to be examined, and returns as scattered light, and guides the light to the optical detector 12 as an optical signal, is determined according to the detection depth D of the object to be examined, so that it is possible to detect the scattered light from the scatterer surface layer at a limited depth with a simple configuration. Thereby, it is possible to measure the scattered light based on a detection depth being equivalent to the detection depth controlled by the spatial coherence length without measuring an interference signal using a plurality of fibers as in the conventional manner. In particular, this is effective when scattering angle information is not required as in the LEBS in the detection depth of the scatterer surface layer.

In the conventional interference signal measurement, a high accuracy is required to arrange the fiber. However, in the scattered light measurement probe 101 according to the present embodiment, the arrangement accuracy as high as that in the conventional measurement is not required, so that it is possible to reduce manufacturing costs.

In the first embodiment described above, it is assumed that the light for mainly obtaining information of a biological tissue is light from visible light to near infrared light. However, the light is not limited to visible light and near infrared light for obtaining information of a biological tissue and other things. The light of measurement target wavelength should be optimized to obtain information of a biological tissue and can be arbitrarily selected according to an object from which information is obtained. It is assumed that the light of measurement target wavelength is set by setting a wider range of the wavelength of the light or discretely setting a plurality of bands when the spectroscopic information is effective and limiting a band to some extent if the spectroscopic information is not effective. Light including the light of measurement target wavelength is generated from the light source and guided into the fiber. When a light flux from the light source is connected to the fiber, if the light flux is concentrated at a far end of the fiber in an optical system in which lenses are combined, the amount of irradiation light increases, so that it is possible to estimate that the measurement quality is improved.

The object to be examined, which is the object to be measured, is irradiated with the light flux guided by the fiber. The object to be examined here is not limited to biological tissue, but any material that scatters/diffuses light, such as a colony of cells and a turbid solution of some materials, may be an object to be measured. The irradiation light interacts with the object to be examined and is scattered. As a result, the irradiation light returns to the original direction. Intensity information of the scattered light is acquired by detecting the scattered return light by the detector.

Second Embodiment

Figure 5:
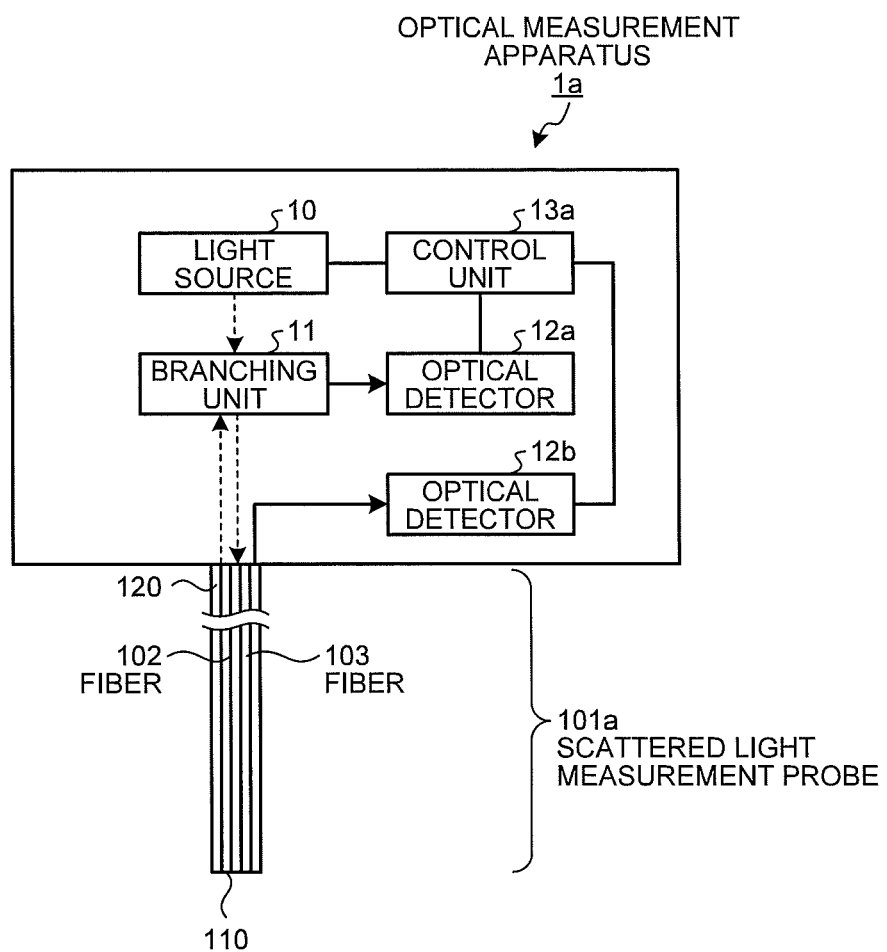
FIG. 5 is a conceptual diagram illustrating an optical measurement apparatus and a scattered light measurement probe according to a second embodiment of the present invention.
Figure 6:
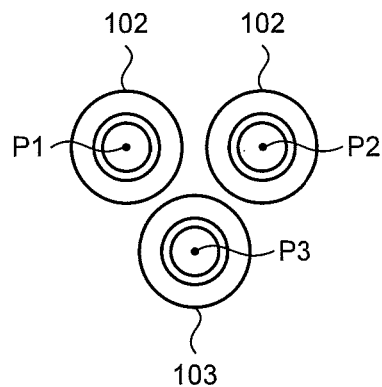
FIG. 6 is a plan view schematically illustrating an arrangement of fibers of the scattered light measurement probe according to the second embodiment of the present invention.

Next, a second embodiment of the present invention will be described. FIG. 5 is a conceptual diagram illustrating an optical measurement apparatus 1a and a scattered light measurement probe 101a according to the second embodiment. FIG. 6 is a plan view schematically illustrating an arrangement of fibers of the scattered light measurement probe 101a according to the second embodiment. The same components as those described in FIG. 1 or the like are given the same reference signs. Although, in the description of the first embodiment, there is only one fiber, a plurality of fibers may be provided to increase the amount of light to be detected. In the second embodiment described below, a plurality of fibers are used.

As illustrated in FIG. 5, the scattered light measurement apparatus including the optical measurement apparatus 1a and the scattered light measurement probe 101a non-invasively detects back-scattered return light from a relatively weak scattering medium such as a biological tissue as information.

The optical measurement apparatus 1a includes a light source 10 that emits light including at least light of measurement target wavelength, a branching unit 11 that concentrates or refracts light from the light source 10 and the scattered light measurement probe 101a and guides the light in a specified direction respectively, an optical detector 12a that detects light, which is received by the scattered light measurement probe 101a through the branching unit 11, an optical detector 12b (second optical detector) that detects light which is received by the scattered light measurement probe 101a, and a control unit 13a that controls the entire optical measurement apparatus 1a and evaluates scattering characteristics of an object to be examined on the basis of the light detected by the optical detector 12a and 12b.

The scattered light measurement probe 101a includes a plurality of fibers 102 described above as in the first embodiment and one or a plurality of fibers 103 (correction fiber) which is provided inside the tube shape, connected to the optical measurement apparatus 1a at a far end 120, receives light, which is irradiated by the fibers 102, propagates inside the object to be examined, and returns as scattered light, at a near end 110, and guides the light to the optical detector 12b as an optical signal. The fiber 103 is formed by using, for example, a step index single core fiber. In the second embodiment, two fibers 102 for propagating illumination light and detected light, and a single fiber 103 (correction fiber) are provided. The light received by the two fibers 102 is collected through the branching unit 11 and guided to the optical detector 12a. As described above, the core diameter D_core of the fiber 102 is defined according to the detection depth D of the object to be examined.

Here, the fibers 102 and 103 are arranged so that centers P1 to P3 of the fibers 102 and 103 are equally distant from each other. It is preferable that the fibers 102 and 103 are arranged to be in contact with each other.

When the control unit 13a evaluates the scattering characteristics of the object to be examined, the control unit 13a calculates a detection intensity $I_D$ on the basis of a signal from the fibers 102 acquired from the optical detector 12a and a signal from the fiber 103 acquired from the optical detector 12b. In the second embodiment, when a signal intensity detected by the optical detector 12a is $I_A$ and a signal intensity detected by the optical detector 12b is $I_B$, the detection intensity $I_D$ is given by $I_D = I_A - I_B$.

Here, the two fibers 102 are arranged adjacent to each other. Therefore, there is a risk that a crosstalk occurs in which a component of light irradiated from one fiber 102 enters the other fiber 102. Thereby, the intensity of the signal intensity $I_A$ increases by the amount of crosstalk with respect to the original signal intensity. The signal intensity $I_B$ is obtained by the fiber 103 receiving light which is irradiated from the two fibers 102, propagates inside the object, and returns as scattered light. Thereby, the signal intensity $I_B$ has an intensity corresponding to the amount of crosstalk by which the signal intensity $I_A$ increases.

Therefore, as described above, the detection intensity $I_D$ is calculated by $I_D = I_A - I_B$, so that it is possible to obtain the signal intensity $I_A$ from which the amount increased by the crosstalk is removed. The control unit 13a evaluates the scattering characteristics of the object to be examined on the basis of the detection intensity $I_D$.

According to the second embodiment described above, in the same manner as in the first embodiment, the core diameter D_core of the fiber 102, which irradiates the object to be examined with at least light of measurement target wavelength, receives light, which is irradiated, propagates inside the object to be examined, and returns as scattered light, and guides the light to the optical detector 12a as an optical signal, is determined according to the detection depth D of the object to be examined, so that it is possible to detect the scattered light from the scatterer surface layer at a limited depth with a simple configuration. Thereby, it is possible to measure the scattered light in depth being equivalent to the detection depth controlled by the spatial coherence length without measuring an interference signal as in the conventional manner.

According to the second embodiment, a plurality of fibers 102 is provided and the fiber 103 for removing crosstalk is provided, so that it is possible to increase the detection intensity of the signals and obtain an accurate detection intensity with respect to the scatterer surface layer at a limited depth with no effect of the crosstalk.

In the second embodiment, the branching unit 11 may include an optical system 111 such as a half mirror according to the each fiber 102 (see FIG. 2), or the branching unit 11 may collectively collect the light from the light source 10, guide the light to the each fiber 102, return the light from the fibers 102 by one half mirror, and guide the light to the optical detector 12a.

Although, in the description of the second embodiment, the fibers 102 and the fiber 103 are arranged so that the distances between the centers of the fibers 102 and the fiber 103 are equivalent, the distances need not be the same as long as the effect of the crosstalk in the signal intensity $I_A$ can be removed by adjusting the signal intensities according to the number of the fibers and the distances between the centers. If the distances are not the same, division is performed on intensity depending on the crosstalk to provide $I_D = I_A - cI_B$ (c is coefficient). The numbers of the fibers 102 and 103 to be arranged can be arbitrarily set.

Figure 7:
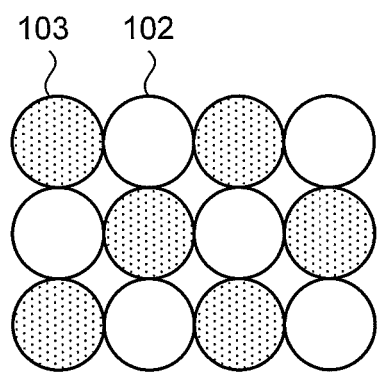
FIG. 7 is a plan view schematically illustrating an arrangement of fibers of a scattered light measurement probe according to a first modified example of the second embodiment of the present invention.
Figure 8:
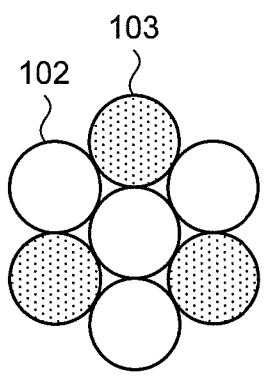
FIG. 8 is a plan view schematically illustrating an arrangement of fibers of a scattered light measurement probe according to a second modified example of the second embodiment of the present invention.

FIG. 7 is a plan view schematically illustrating an arrangement of the fibers 102 and 103 of the scattered light measurement probe according to a first modified example of the second embodiment. FIG. 8 is a plan view schematically illustrating an arrangement of the fibers 102 and 103 of the scattered light measurement probe according to a second modified example of the second embodiment.

For example, as illustrated in FIG. 7, the fibers 102 and 103 may be arranged in a grid pattern. In this case, it is preferable to arrange the fibers 102 and 103 to be adjacent to each other by considering that the signal intensity according to the crosstalk between the fibers 102 is acquired by the fiber 103.

As illustrated in FIG. 8, three fibers 102 and three fibers 103 may be alternately arranged around a fiber 102 arranged at the center. Thereby, the distance between the fiber 102 and the fiber 103 adjacent to each other can be equivalent.

Third Embodiment

Figure 9:
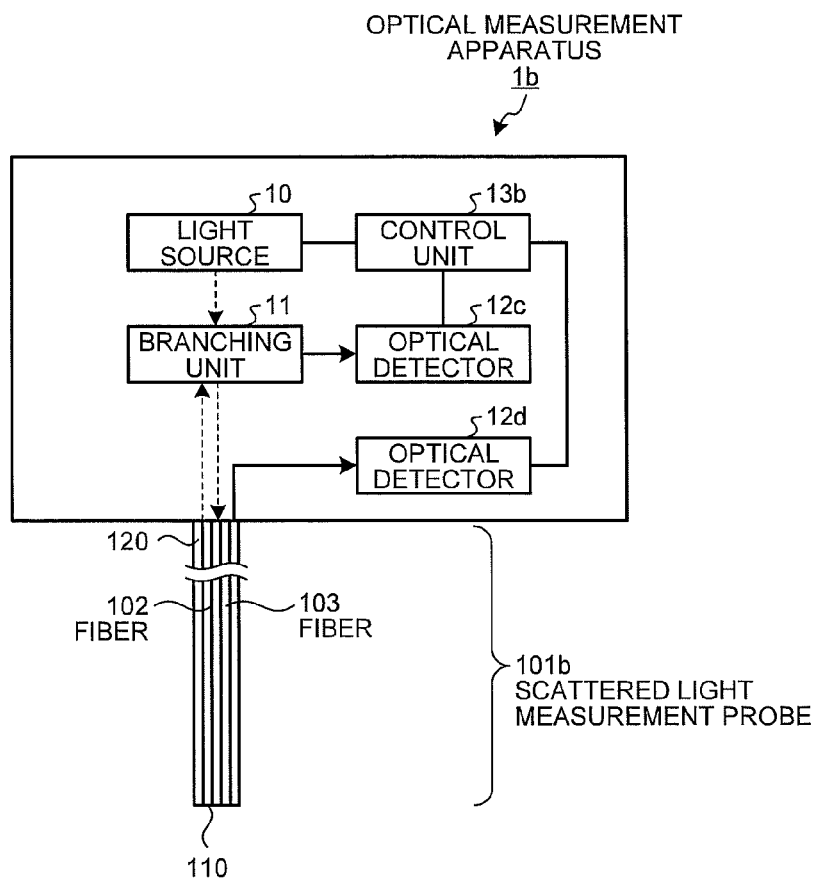
FIG. 9 is a conceptual diagram illustrating an optical measurement apparatus and a scattered light measurement probe according to a third embodiment of the present invention.
Figure 10:
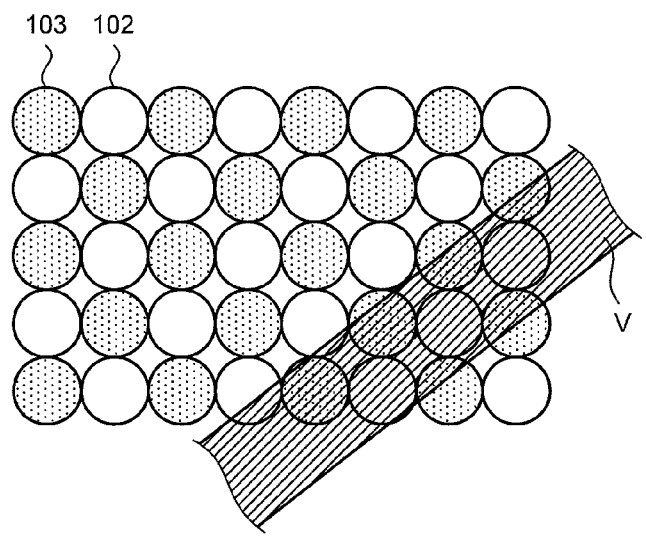
FIG. 10 is a diagram schematically illustrating an arrangement of fibers of the scattered light measurement probe according to the third embodiment of the present invention.

Next, a third embodiment of the present invention will be described. FIG. 9 is a conceptual diagram illustrating an optical measurement apparatus 1b and a scattered light measurement probe 101b according to the third embodiment. FIG. 10 is a plan view schematically illustrating fibers of the scattered light measurement probe 101b according to the third embodiment. The same components as those described in FIG. 1 or the like are given the same reference signs. Although, in the description of the second embodiment, a plurality of fibers is provided to increase the amount of light to be detected, further, the method of calculating the signal intensity may be changed according to the signal intensities of the each fiber.

As illustrated in FIG. 9, the scattered light measurement apparatus including the optical measurement apparatus 1b and the scattered light measurement probe 101b non-invasively detects back-scattered return light from a relatively weak scattering medium such as a biological tissue as information.

The optical measurement apparatus 1b includes a light source 10 that emits light including at least light of measurement target wavelength, a branching unit 11 that concentrates or refracts light from the light source 10 and the scattered light measurement probe 101b and guides the light in a specified direction respectively, an optical detector 12c that detects light, which is received by the scattered light measurement probe 101b through the branching unit 11, an optical detector 12d (second optical detector) that detects light which is received by the scattered light measurement probe 101b, and a control unit 13b that controls the entire optical measurement apparatus 1b and evaluates scattering characteristics of an object to be examined on the basis of the light detected by the optical detectors 12c and 12d.

The scattered light measurement probe 101b includes a plurality of the fibers 102 described above and a plurality of the fibers 103 described above. The fibers 102 and 103 are arranged to be in contact with each other in a grid pattern. In the third embodiment, the light received by the each fiber 102 is guided to the optical detector 12c through the branching unit 11. As described above, the core diameter D_core of the fiber 102 is defined according to the detection depth D of the object to be examined.

The optical detectors 12c and 12d detect the scattered light received by the plurality of fibers 102 and 103. The optical detectors 12c and 12d are realized by using an image sensor such as a CCD or a two-dimensional sensor such as an area sensor. The optical detectors 12c and 12d detect light received by the fibers 102 and 103 for the each fiber. Optical signals detected by the optical detectors 12c and 12d are stored by the control unit 13b as signals (signal intensities) necessary for measurement.

When the control unit 13b evaluates the scattering characteristics of the object to be examined, the control unit 13b calculates a detection intensity $I_D'$ on the basis of signals from the fibers 102 acquired from the optical detector 12c and signals from the fibers 103 acquired from the optical detector 12d. In this case, it is assumed that the signal intensities of the each fiber 102 detected by the optical detector 12c are $I_A'$ and the signal intensities of the each fiber 103 detected by the optical detector 12d are $I_B'$.

When there is an object which decreases the detection intensity, such as a blood vessel V which has a light absorption property, in an arrangement area of the fibers 102 and 103 in the surface layer 2 of the object to be examined, the amount of light received by the fibers 102 and 103 significantly decreases. In this case, it is possible to check the signal intensities $I_A'$ and $I_B'$ acquired by the optical detectors 12c and 12d from the fibers 102 and 103 for the each fiber, so that it is possible to recognize that there are fibers where the intensity is decreased by the blood vessel V.

The control unit 13b calculates the sum of the signal intensities $I_A'$ acquired from the fibers 102 after removing the signal intensities acquired from the fibers 102 where the intensity is decreased by the blood vessel V from all the signal intensities $I_A'$ acquired from the each fiber 102. Also, the control unit 13b calculates the sum of the signal intensities $I_B'$ acquired from the fibers 103 after removing the signal intensities acquired from the fibers 103 where the intensity is decreased by the blood vessel V from all the signal intensities $I_B'$ acquired from the each fiber 103. Here, it is assumed that the calculated sum of the signal intensities of the fibers 102 is $I_A''$ and the calculated sum of the signal intensities of the fibers 103 is $I_B''$.

In this case, the control unit 13b determines whether or not the signal intensities $I_A'$ and $I_B'$ are greater than a set threshold value and determines that signal intensities smaller than the threshold value are the signal intensities which are decreased by the blood vessel V. Here, for example, the control unit 13b sets a signal intensity of 80% of the maximum value of the signal intensities $I_A'$ and $I_B'$ as the threshold value. The control unit 13b may acquire a specified number of signal intensities $I_A'$ and $I_B'$ in order from the greatest signal intensity.

Thereby, in the same manner as in the second embodiment, the detection intensity $I_D'$ is calculated by $I_D' = I_A'' - I_B''$, so that it is possible to obtain the signal intensity $I_A''$ from which the amount increased by the crosstalk is removed and from which the signal intensities decreased by the blood vessel V or the like are removed. The control unit 13b evaluates the scattering characteristics of the object to be examined on the basis of the detection intensity $I_D'$.

According to the third embodiment described above, in the same manner as in the first embodiment, the core diameter D_core of the fiber 102, which irradiates the object to be examined with at least light of measurement target wavelength, receives light, which is irradiated, propagates inside the object to be examined, and returns as scattered light, and guides the light to the optical detector 12c as an optical signal, is determined according to the detection depth of the object to be examined, so that it is possible to detect the scattered light from the scatterer surface layer at a limited depth with a simple configuration. Thereby, it is possible to measure the scattered light in depth being equivalent to the detection depth controlled by the spatial coherence length without measuring an interference signal as in the conventional manner.

According to the third embodiment, a plurality of fibers 102 is provided and the fibers 103 for removing crosstalk are provided, and the detection intensity is acquired by detecting the signal intensities for the each fiber 102 and 103 and removing the signal intensities decreased by the blood vessel V or the like, so that it is possible to increase the detection intensity of the signals and obtain an accurate detection intensity with respect to the scatterer surface layer at a limited depth with no effect of the crosstalk.

Fourth Embodiment

Figure 11:
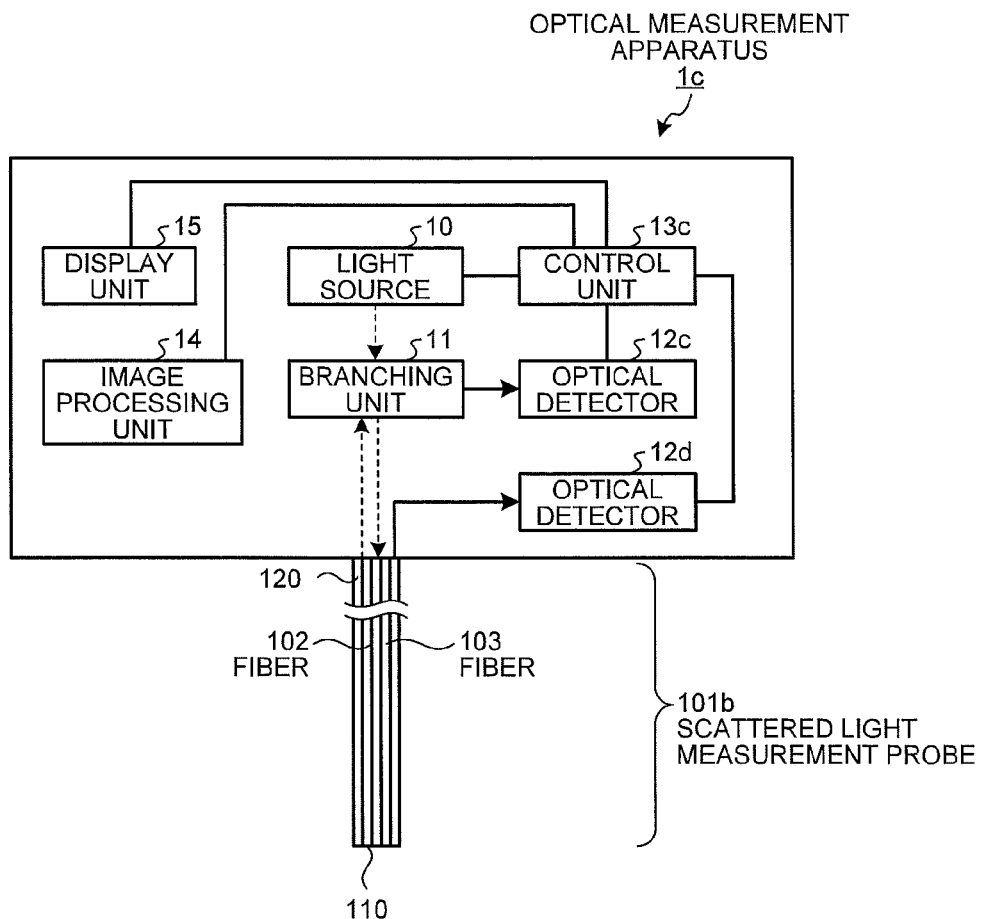
FIG. 11 is a conceptual diagram illustrating an optical measurement apparatus and a scattered light measurement probe according to a fourth embodiment of the present invention.
Figure 12:
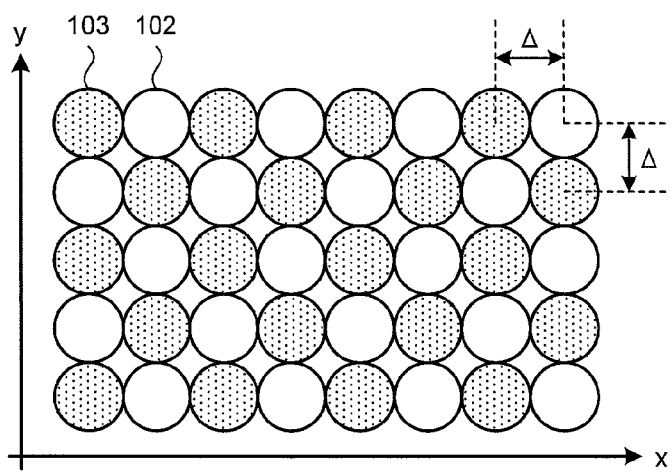
FIG. 12 is a diagram schematically illustrating an arrangement of fibers of the scattered light measurement probe according to the fourth embodiment of the present invention.
Figure 13:
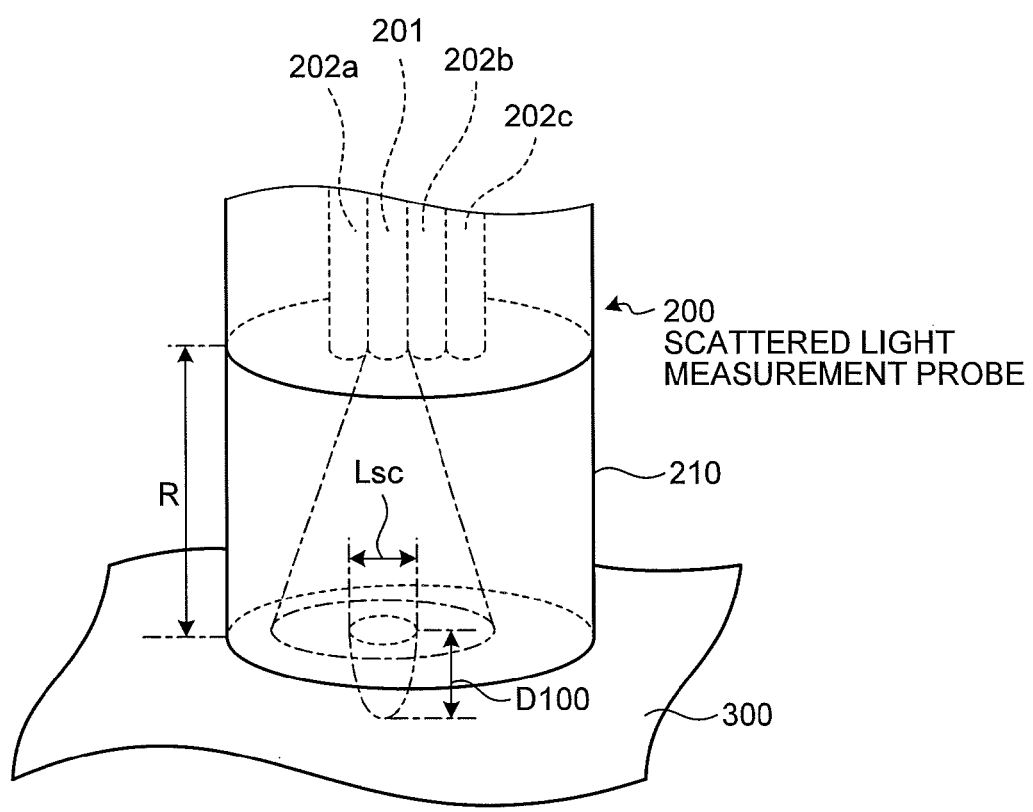
FIG. 13 is a schematic diagram illustrating a main part of a conventional scattered light measurement probe.

Next, a fourth embodiment of the present invention will be described. FIG. 11 is a conceptual diagram illustrating an optical measurement apparatus 1c and a scattered light measurement probe 101b according to the fourth embodiment. FIG. 12 is a plan view schematically illustrating fibers of the scattered light measurement probe 101b according to the fourth embodiment. The same components as those described in FIG. 1 or the like are given the same reference signs. Although, in the description of the third embodiment, a plurality of fibers is provided and a signal intensity is detected for the each fiber, further, image processing may be performed on the basis of the signal intensities of the fibers and an image may be displayed.

As illustrated in FIG. 11, the scattered light measurement apparatus including the optical measurement apparatus 1c and the scattered light measurement probe 101b described above non-invasively detects back-scattered return light from a relatively weak scattering medium such as a biological tissue as information.

The optical measurement apparatus 1c includes a light source 10 that emits light including at least light of measurement target wavelength, a branching unit 11 that concentrates or refracts light from the light source 10 and the scattered light measurement probe 101b and guides the light in a specified direction respectively, an optical detector 12c that detects light, which is received by the scattered light measurement probe 101b through the branching unit 11, an optical detector 12d that detects light which is received by the scattered light measurement probe 101b, a control unit 13c that controls the entire optical measurement apparatus 1c and evaluates scattering characteristics of an object to be examined on the basis of the light detected by the optical detectors 12c and 12d, an image processing unit 14 that performs image processing on signals based on the signal intensities detected by the optical detectors 12c and 12d, and a display unit 15 that displays image signals processed by the image processing unit 14 as an image. The display unit 15 is realized by, for example, a monitor.

The optical detectors 12c and 12d respectively detect the scattered light received by the plurality of fibers 102 and 103. The optical detectors 12c and 12d are realized by using an image sensor such as a CCD or a two-dimensional sensor such as an area sensor. The optical detectors 12c and 12d detect light received by the fibers 102 and 103 for the each fiber. Optical signals detected by the optical detectors 12c and 12d are stored by the control unit 13c as signals (signal intensities) necessary for measurement.

When the control unit 13c evaluates the scattering characteristics of the object to be examined, the control unit 13c calculates the detection intensity $I_D''$ described above on the basis of signals from the fibers 102 acquired from the optical detector 12c and signals from the fibers 103 acquired from the optical detector 12d and evaluates the scattering characteristics of the object to be examined on the basis of the detection intensity $I_D''$.

When it is assumed that the signal intensities of the each fiber 102 detected by the optical detector 12c are $I_A'$ and the signal intensities of the each fiber 103 detected by the optical detector 12d are $I_B'$, the image processing unit 14 performs image processing on the basis of the signal intensities $I_A'$ and $I_B'$. Here, the signal intensities $I_A'$ and $I_B'$ are given information of the position (x, y) of the fibers 102 and 103 respectively by the control unit 13c. In other words, the each signal intensities $I_A'$ and $I_B'$ can be replaced by $I_A'=A(x, y)$ and $I_B'=B(x, y)$ as signal intensities according to the position (x, y). The image processing unit 14 constructs an image based on the coordinate information and the signal intensities and displays the image as image signals.

Here, the control unit 13c calculates the detection intensity $I_D''$ of a certain fiber 102 on the basis of the formula (2) below.

$$I_D''=A(x,y)-(B(x+\Delta,y)+B(x-\Delta,y)+B(x,y+\Delta)+B(x,y-\Delta))/4 \quad (2)$$

By the formula (2), it is possible to obtain the detection intensity $I_D''$ which is the signal intensity $I_A'$ from which the amount increased by the crosstalk is removed. The control unit 13a evaluates the scattering characteristics of the object to be examined on the basis of the detection intensity $I_D''$. The control unit 13a may evaluate the scattering characteristics of the object to be examined on the basis of the sum of the detection intensities $I_D''$ of the fibers 102.

According to the fourth embodiment described above, in the same manner as in the first embodiment, the core diameter D_core of the fiber 102, which irradiates the object to be examined with at least light of measurement target wavelength, receives light, which is irradiated, propagates inside the object to be examined, and returns as scattered light, and guides the light to the optical detector 12c as an optical signal, is determined according to the detection depth of the object to be examined, so that it is possible to detect the scattered light from the scatterer surface layer at a limited depth with a simple configuration. Thereby, it is possible to measure the scattered light in depth being equivalent to the detection depth controlled by the spatial coherence length without measuring an interference signal as in the conventional manner.

According to the fourth embodiment, the signal intensity is detected for the each fiber 102 and 103, each signal intensity has coordinate information, and the image processing unit 14 constructs an image, so that it is possible to acquire the detection intensity for evaluating the scattering characteristics of the object to be examined and display the optical signals from the fibers 102 and 103 as an image.

According to the fourth embodiment, a plurality of fibers 102 is provided and the fibers 103 for removing crosstalk are provided, so that it is possible to increase the detection intensity of the signals and obtain an accurate detection intensity with respect to the scatterer surface layer at a limited depth with no effect of the crosstalk.

According to some embodiments, because a core diameter of a fiber that: irradiates an object to be examined with at least light of a measurement target wavelength; receives light, which has been irradiated, propagated inside the object to be examined, and returned thereto as scattered light; and guides the light to the optical detector as an optical signal, is determined according to a detection depth of the object to be examined, it is possible to detect scattered light from a scatterer surface layer at a limited depth by a simple structure.

INDUSTRIAL APPLICABILITY

As described above, a scattered light measurement apparatus according to some embodiments is useful for detecting scattered light from a scatterer surface layer at a limited depth by a simple structure.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A scattered light measurement apparatus, comprising:
an optical measurement apparatus to and from which light is input and output and which is configured to perform measurement of input light; and
a scattered light measurement probe configured to irradiate an object to be examined with light from the optical measurement apparatus, configured to receive light from the object to be examined, and configured to output the received light to the optical measurement apparatus, wherein
the optical measurement apparatus includes:
   a light source configured to emit light including at least light of a measurement target wavelength;
   first and second optical detectors configured to detect the light received by the scattered light measurement probe;
   a brancher configured to guide the light from the light source to the scattered light measurement probe and guide the light from the scattered light measurement probe to the first and second optical detectors; and
   a controller configured to evaluate scattering characteristics of a surface layer of the object to be examined based on the light detected by the first and second optical detectors,
the scattered light measurement probe includes:
   two or more first fibers that are connected to the optical measurement apparatus at one end thereof, configured to propagate the light from the light source to irradiate the object to be examined, configured to come in contact with the object to be examined at another end thereof, configured to receive the light that has irradiated the object to be examined, propagated inside the object to be examined, and returned thereto, and configured to guide the received light as an optical signal to the first optical detector through the brancher; and
   a second fiber configured to receive the light that has been irradiated by the two or more first fibers, propagated inside the object to be examined, and returned thereto, and configured to guide the received light as an optical signal to the second optical detector through the brancher, wherein the second fiber does not propagate the light from the light source, wherein
each of the two or more fibers has a diameter determined according to a detection depth of the object to be examined, and
the controller is configured to evaluate the scattering characteristics based on signal intensities of the optical signal detected by the first optical detector and the optical signal detected by the second optical detector.

2. The scattered light measurement apparatus according to claim 1, further comprising:
one or more additional second fibers, wherein
   the first optical detector is configured to detect the signal intensity for each of the two or more fibers,
   the second optical detector is configured to detect the signal intensity for each of the second fiber and the one or more additional second fibers, and
   the controller is configured to evaluate the scattering characteristics based on the signal intensities greater than a set threshold value.

3. The scattered light measurement apparatus according to claim 1, further comprising:
one or more additional second fibers, wherein
   the first optical detector is configured to detect the signal intensity for each of the two or more first fibers,
   the second optical detector is configured to detect the signal intensity for each of the second fiber and the one or more additional second fibers,
   the controller is configured to assign positional information to each signal intensity, and
   the optical measurement apparatus includes an image processor configured to perform image processing based on the signal intensities.

4. The scattered light measurement apparatus according to claim 1, wherein
   as the two or more first fibers and the second fiber, two first fibers and a single second fiber are provided,
   the two first fibers and the single second fiber are arranged such that centers thereof are equally distant from each other.

* * * * *